(12) United States Patent
Krivitski et al.

(10) Patent No.: US 11,633,525 B2
(45) Date of Patent: Apr. 25, 2023

(54) METHOD AND APPARATUS FOR ASSESSING CARDIAC OUTPUT IN VENO-ARTERIAL EXTRACORPOREAL BLOOD OXYGENATION

(71) Applicant: TRANSONIC SYSTEMS INC., Ithaca, NY (US)

(72) Inventors: Nikolai M. Krivitski, Ithaca, NY (US); Gregory Galyanov, Ithaca, NY (US)

(73) Assignee: Transonic Systems Inc., Ithaca, NY (US)

( * ) Notice: Subject to any disclaimer, the term of this patent is extended or adjusted under 35 U.S.C. 154(b) by 601 days.

(21) Appl. No.: 16/776,050

(22) Filed: Jan. 29, 2020

(65) Prior Publication Data
US 2020/0237992 A1 Jul. 30, 2020

Related U.S. Application Data

(60) Provisional application No. 62/798,269, filed on Jan. 29, 2019.

(51) Int. Cl.
*A61M 1/16* (2006.01)
(52) U.S. Cl.
CPC ........ *A61M 1/1647* (2014.02); *A61M 1/1698* (2013.01); *A61M 2202/0208* (2013.01); *A61M 2205/33* (2013.01); *A61M 2230/20* (2013.01)
(58) Field of Classification Search
CPC ........... A61B 5/14551; A61B 5/14557; A61M 1/1647; A61M 1/1698; A61M 1/3666;
(Continued)

(56) References Cited

U.S. PATENT DOCUMENTS 5,092,357 A  3/1992 Chapman et al.
5,267,417 A  12/1993 Rose
(Continued)

FOREIGN PATENT DOCUMENTS

JP  2008538934 A  11/2008
JP  2015529116 A  10/2015
(Continued)

OTHER PUBLICATIONS

International Preliminary Report on Patentability from corresponding international application PCT/US2020/015666 (Year: 2020).*
(Continued)

*Primary Examiner* — Benjamin J Klein
(74) *Attorney, Agent, or Firm* — Brian Shaw, Esq.; Harter Secrest & Emery LLP

(57) ABSTRACT

A system for calculating cardiac output (CO) of a patient undergoing veno-arterial extracorporeal oxygenation includes measuring first oxygenated blood flow rate by a pump in the extracorporeal blood oxygenation circuit as introduced into an arterial portion of the patient circulation system and a corresponding arterial oxygen saturation, then changing the pump flow rate, such as decreasing, to produce a corresponding change in arterial oxygen saturation (wherein such change is outside of normal operating variances, operating errors or drift), which change in the arterial oxygen saturation is measured. From the first flow rate and the second flow rate along with the corresponding measured arterial oxygen saturation, the CO of the patient can be calculated, without reliance upon a measure of venous oxygen saturation. Alternatively, the CO of the patient can be calculated, without reliance upon a change in flow rate by changing a gas exchange with the blood in the extracorporeal blood oxygenation circuit to impart corresponding changes in a blood parameter in the arterial portion of the
(Continued)

patient circulation system and the blood delivered from the extracorporeal blood oxygenation circuit.

17 Claims, 3 Drawing Sheets

(58) Field of Classification Search
CPC ...... A61M 2202/0208; A61M 2205/33; A61M 2205/3334; A61M 2230/20; A61M 2230/202; A61M 2230/205
See application file for complete search history.

(56) References Cited

U.S. PATENT DOCUMENTS

| | | | |
|---|---|---|---|
| 5,398,461 A | 3/1995 | Rose | |
| 5,437,296 A | 8/1995 | Citino | |
| 5,474,097 A | 12/1995 | Lowe et al. | |
| 5,685,989 A | 11/1997 | Krivitski et al. | |
| 5,928,180 A | 7/1999 | Krivitski et al. | |
| 6,090,061 A | 7/2000 | Steuer et al. | |
| 6,155,984 A | 12/2000 | Krivitski | |
| 6,461,231 B1 | 10/2002 | Taylor et al. | |
| 6,506,146 B1 | 1/2003 | Mohl | |
| 6,616,615 B2 * | 9/2003 | Mault | A61B 5/029 600/538 |
| 11,439,735 B2 | 9/2022 | Krivitski et al. | |
| 11,446,438 B2 * | 9/2022 | Sowb | A61M 1/1613 |
| 2002/0022785 A1 | 2/2002 | Romano | |
| 2004/0158133 A1 | 8/2004 | Krivitski et al. | |
| 2006/0052715 A1 * | 3/2006 | Krivitski | A61B 5/0275 600/508 |
| 2006/0211947 A1 * | 9/2006 | Krivitski | A61B 5/0275 600/526 |
| 2008/0033314 A1 | 2/2008 | Krivitski | |
| 2010/0057046 A1 | 3/2010 | Stevens et al. | |
| 2014/0276071 A1 | 9/2014 | Hunziker et al. | |
| 2015/0314059 A1 | 11/2015 | Federspiel et al. | |
| 2015/0316404 A1 | 11/2015 | Krivitski et al. | |
| 2016/0000989 A1 | 1/2016 | Haag et al. | |
| 2016/0346448 A1 * | 12/2016 | Kaiser | A61N 1/36528 |
| 2017/0239407 A1 | 8/2017 | Hayward | |
| 2018/0353680 A1 | 12/2018 | Hatib et al. | |
| 2019/0030232 A1 | 1/2019 | Kreymann et al. | |
| 2019/0083694 A1 | 3/2019 | Kopperschmidt et al. | |
| 2019/0083789 A1 | 3/2019 | Thakur et al. | |
| 2020/0306437 A1 | 10/2020 | Sternby et al. | |
| 2020/0345915 A1 | 11/2020 | Krivitski et al. | |

FOREIGN PATENT DOCUMENTS

| | | |
|---|---|---|
| JP | 2017217296 A | 12/2017 |
| WO | 2006096758 A2 | 9/2006 |
| WO | 2006096758 A3 | 9/2006 |

OTHER PUBLICATIONS

Abrams et al. (2015) "Identification and management of recirculation in venovenous ECMO," Extracorporeal Life Support Organization (ELSO): 1-7.

Broman et al. (2015) "Recirculation During Veno-Venous Extra-Corporeal Membrane Oxygenation—A Simulation Study," The International Journal of Artificial Organs 38(1): 23-30.

Joyce et al. (2018) "A mathematical model of CO2, 02 and N2 exchange during venovenous extracorporeal membrane oxygenation," Intensive Care Medicine Experimental 6(25): 1-13.

Mendes et al. (2016) "Kinetics of arterial carbon dioxide during veno-venous extracorporeal membrane oxygenation support in an apnoeic porcine model," Intensive Care Medicine Experimental 4(1): 1-11.

Messai et al. 2013 (published online Dec. 5, 2012) "A New Formula For Determining Arterial Oxygen Saturation During Venovenous Extracorporeal Oxygenation," Intensive Care Medicine 39: 327-334.

Nassar et al. (Jun. 2017) "Estimating Arterial Partial Pressure of Carbon Dioxide in Ventilated Patients: How Valid Are Surrogate Measures?", American Thoracic Society 14(6): 1005-1014.

Nunes et al. (2014) "Severe Hypoxemia During Veno-Venous Extracorporeal Membrane Oxygenation: Exploring the Limits of Extracorporeal Respiratory Support", Clinic 69(3): 173-178.

Romano et al. (2017) "Extracorporeal respiratory support in adult patients," Jornal Brasileiro de Pneumologia 43(1): 60-70.

Transonic Systems Inc. (2015) "Best Practices in Hemodialysis," Handbook: 80 pgs.

Walker et al. (2009) "Calculating Mixed Venous Saturation during Veno-Venous Extracorporeal Membrane Oxygenation," Perfusion 24(5): 333-339.

Bachmann et al. (2020) "Gas exchange calculation may estimate changes in pulmonary blood flow during veno-arterial extracorporeal membrane oxygenation in a porcine model," American Journal of Physiology-Lung Cellular and Molecular Physiology 318(6): 1-41.

* cited by examiner

METHOD AND APPARATUS FOR ASSESSING CARDIAC OUTPUT IN VENO-ARTERIAL EXTRACORPOREAL BLOOD OXYGENATION

CROSS-REFERENCE TO RELATED APPLICATIONS

The present application claims the benefit of U.S. Provisional patent application Ser. No. 62/798,269 filed Jan. 29, 2019 entitled METHOD AND APPARATUS FOR ASSESSING CARDIAC OUTPUT IN VENO-ARTERIAL EXTRACORPOREAL BLOOD OXYGENATION and which is hereby expressly incorporated by reference.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

REFERENCE TO A SEQUENCE LISTING

Not applicable.

STATEMENT REGARDING PRIOR DISCLOSURES BY THE INVENTOR OR A JOINT INVENTOR

Not applicable.

BACKGROUND OF THE INVENTION

The present disclosure relates to assessing cardiac output of a patient operably connected to a veno-arterial (VA) extracorporeal circuit, and particularly a veno-arterial extracorporeal blood oxygenation circuit such as, but not limited to, a veno-arterial extracorporeal membrane oxygenation (ECMO) circuit.

VA ECMO is a medical procedure employed in patients who have a heart failure and in some cases also experiencing life-threatening respiratory failure, typically Acute Respiratory Distress Syndrome (ARDS). Patients may also need VA ECMO after heart surgery if the heart does not recover. The combination of lung and heart failure is often observed in prematurely born neonates.

The lack of oxygen delivery due to low cardiac output (CO) and compromised lung performance causes damage to the tissue and can ultimately lead to the death of the patient. Extracorporeal blood oxygenation, such as VA ECMO, supplements or replaces blood oxygenation by the lungs and supplants the heart of the patient.

In VA ECMO, a large venous (access) cannula is inserted usually through the jugular (or the femoral) vein with the cannula tip located near the right atrium to withdraw blood. These cannulae are then connected to an extracorporeal circuit which includes a pump and a membrane oxygenator. In children and in some adults, blood is usually delivered back to the patient in the ascending aorta. Also, adults often have the blood withdrawn via a femoral venous (access) catheter with a tip close to the right atria and delivered via a femoral arterial (return) catheter with a tip in the descending aorta.

There are multiple variations of connection, however, in each the patient blood is continuously circulated through the extracorporeal circuit by being withdrawn from the patient, then circulated through an oxygenator, such as a membrane oxygenator, where the blood is oxygenated. Then the blood is returned to the patient where the now oxygenated blood is pumped into the aorta where it mixes with blood coming from the heart.

While cardiopulmonary support offers life-saving and life prolonging treatment, the intrusive nature of the cardiopulmonary VA ECMO support carries significant risks and potential complications. Each additional hour of unnecessary VA ECMO cardiopulmonary support increases the probability of negative complications like bleeding and clotting as well as increasing the already substantial costs of the treatment. Therefore, it is desirable to limit the duration of cardiopulmonary support as required by the individual patient. One of the main criteria for decreasing or terminating cardiopulmonary support is an adequate increase in the ability of the heart to pump blood, that is the cardiac output increases. Thus, the earlier that a physician can identify the recovery of the heart, the faster the patient can be removed from VA ECMO, if the lungs have also recovered. Alternatively, if the heart has recovered but the lungs have not recovered or remain problematic, such as not providing sufficient oxygenation, the patient can be moved to VV ECMO, which is a more stable procedure and the patient can be on VV ECMO for a longer duration, especially for patients having a sufficiently working heart.

Current standard methods to measure cardiac output (CO) include (i) pulmonary artery thermodilution which is invasive and cannot be used in small children, and (ii) transpulmonary thermodilution which is also invasive and typically has less accuracy in the VA ECMO setting.

Therefore, the need exists for improved systems and methods of measuring cardiac output (CO) during veno-arterial extracorporeal blood oxygenation.

BRIEF SUMMARY OF THE INVENTION

Generally, the present disclosure provides a non-invasive methods and apparatus to measure cardiac output (CO), in a patient operably connected to a veno-arterial extracorporeal circuit, and particularly a veno-arterial extracorporeal blood oxygenation circuit such as but not limited to a veno-arterial extracorporeal membrane oxygenation (VA ECMO) circuit.

In one configuration, a first flow rate from a pump in an extracorporeal circuit and an arterial oxygen saturation are measured, then the pump flow rate is changed, such as decreased (or increased), to produce a corresponding change in arterial oxygen saturation (such change being outside of normal operating variances, operating error or drift), and the second flow rate from the pump and the new arterial oxygen saturation are recorded. From the first pump flow rate, the second pump flow rate and the corresponding first and second arterial oxygen saturation corresponding to the first pump flow rate and the second pump flow rate, the CO of the patient can be calculated.

In another configuration, a method is provided for calculating cardiac output of a patient undergoing veno-arterial extracorporeal oxygenation, wherein the method includes withdrawing blood from a first venous portion of a patient circulation system to pass the withdrawn blood into a veno-arterial extracorporeal blood oxygenation circuit, the veno-arterial extracorporeal circuit having an access line, a return line and a blood oxygenator intermediate the access line and the return line, such that the withdrawn blood enters the extracorporeal blood oxygenation circuit through the access line; pumping the withdrawn blood through the access line and the blood oxygenator to form oxygenated blood; pumping the oxygenated blood from the oxygenator and through the return line; introducing the oxygenated blood from the return line to an arterial portion of the patient circulation system; measuring a first blood flow rate through the extracorporeal blood oxygenation circuit (one of the access line, the blood oxygenator and the return line); measuring an arterial oxygen saturation of the patient during the first blood flow rate; measuring a venous oxygen saturation (or surrogate parameter) of the patient during the first blood flow rate; and calculating a cardiac output of the patient corresponding to the measured blood flow rate, the measured arterial oxygen saturation and the measured venous oxygen saturation.

In a further configuration, the present disclosure provides a method for assessing cardiac output of a patient undergoing veno-arterial extracorporeal blood oxygenation, wherein the method includes establishing a first blood flow rate from an extracorporeal blood oxygenation circuit into an arterial portion of a patient circulation system; measuring the first blood flow rate; measuring a first arterial oxygen saturation of the patient corresponding to the first blood flow rate; establishing a second blood flow rate from the extracorporeal blood oxygenation circuit into the arterial portion of the patient circulation system; measuring the second blood flow rate; measuring a second arterial oxygen saturation of the patient corresponding the second blood flow rate; and calculating a cardiac output of the patient corresponding to the first blood flow rate, the second blood flow rate, the first arterial oxygen saturation and the second arterial oxygen saturation.

A further method is disclosed for calculating cardiac output of a patient undergoing veno-arterial extracorporeal oxygenation, the method including withdrawing blood from a venous portion of a patient circulation system to pass the withdrawn blood into a veno-arterial extracorporeal blood oxygenation circuit, the veno-arterial extracorporeal blood oxygenation circuit having an access line, a return line and a blood oxygenator intermediate the access line and the return line, such that the withdrawn blood enters the veno-arterial extracorporeal blood oxygenation circuit through the access line and returns to the patient circulation system through the return line; passing the withdrawn blood through the access line and the blood oxygenator to form oxygenated blood; passing the oxygenated blood from the oxygenator and through the return line; introducing the oxygenated blood from the return line to an arterial portion of the patient circulation system; measuring a first blood flow rate through the extracorporeal blood oxygenation circuit; measuring an arterial oxygen saturation of the patient; measuring a venous oxygen saturation of the patient; and calculating a cardiac output of the patient corresponding to the measured blood flow rate, the measured arterial oxygen saturation and the measured venous oxygen saturation.

The present disclosure further provides an apparatus for calculating cardiac output of a patient operably connected to a veno-arterial extracorporeal blood oxygenation circuit, the extracorporeal blood oxygenation circuit having an access line withdrawing blood from a circulation system of the patient, a blood oxygenator, a pump and a return line returning oxygenated blood to an arterial portion of the circulation system, wherein the apparatus includes a controller configured to connect to one of the blood oxygenator and the pump, the controller configured to calculate a cardiac output of the patient based on a measured first flow rate of oxygenated blood from the extracorporeal blood oxygenation circuit, a first arterial oxygen saturation of the patient during the first flow rate, a measured second flow rate of oxygenated blood from the extracorporeal blood oxygenation circuit and a second arterial oxygen saturation of the patient during the second flow rate.

Also provided is a method for assessing cardiac output of a patient undergoing veno-arterial extracorporeal blood oxygenation, wherein the method includes measuring a blood flow rate of oxygenated blood delivered to an arterial portion of a patient circulation system by an extracorporeal blood oxygenation circuit; measuring an arterial oxygen saturation of the patient during the first flow rate; measuring a venous oxygen saturation of the patient during the first flow rate; and calculating a cardiac output of the patient corresponding to the measured blood flow rate, the measured arterial oxygen saturation and the measured venous oxygen saturation.

A further method is provide for assessing cardiac output of a patient undergoing veno-arterial extracorporeal blood oxygenation, wherein the method includes establishing a first blood flow rate from an extracorporeal blood oxygenation circuit into an arterial portion of a patient circulation system; measuring the first blood flow rate; measuring a first value of a blood parameter in an arterial portion of the patient circulation system corresponding to the first blood flow rate; establishing a second blood flow rate from the extracorporeal blood oxygenation circuit into the arterial portion of the patient circulation system; measuring the second blood flow rate; measuring a second value of the blood parameter in the arterial portion of the patient circulation system corresponding to the second blood flow rate; and calculating a cardiac output of the patient corresponding to the first blood flow rate, the second blood flow rate, the first value of the blood parameter, and the second value of the blood parameter. It is understood the method can further include measuring the first value of the blood parameter during the first blood flow rate from the extracorporeal blood oxygenation circuit; or wherein measuring the first value of the blood parameter corresponding to the first blood flow rate includes measuring the first value of the blood parameter in an arterial portion of the patient circulation system; or wherein measuring the first value of the blood parameter corresponding to the first blood flow rate includes measuring a first arterial oxygen saturation or wherein measuring the first value of the blood parameter corresponding to the first blood flow rate includes measuring a first arterial oxygen saturation in an arterial portion of the patient circulation system.

An apparatus is provided for quantifying a cardiac output of a patient operably connected to an extracorporeal blood oxygenation circuit, the extracorporeal blood oxygenation circuit having an access line withdrawing blood from a circulation system of the patient, a blood oxygenator, a pump and a return line returning oxygenated blood to an arterial portion of the circulation system, the apparatus including a controller configured to connect to one of the blood oxygenator and the pump, the controller configured to calculate a cardiac output of the patient based on a measured first flow rate of oxygenated blood from the extracorporeal circuit into the patient circulation system, a first arterial oxygen saturation of the patient during the first flow rate, a measured second flow rate of oxygenated blood from the extracorporeal circuit into the patient circulation system and a second arterial oxygen saturation of the patient during the second flow rate.

A further apparatus is provided for quantifying a cardiac output of a patient operably connected to an extracorporeal blood oxygenation circuit, the extracorporeal blood oxygenation circuit having an access line withdrawing blood from a circulation system of the patient, a blood oxygenator, a pump and a return line returning oxygenated blood to an arterial portion of the patient circulation system, the apparatus including a controller, the controller connected to one of the blood oxygenator and the pump, the controller further connected to an oximeter and configured to calculate a cardiac output of the patient corresponding to a measured blood flow rate in the extracorporeal blood oxygenation circuit, a measured arterial oxygen saturation by the oximeter and a measured venous oxygen saturation.

An alternative method is disclosed for calculating cardiac output of a patient undergoing veno-arterial extracorporeal blood oxygenation, the method including establishing a first blood flow rate from an extracorporeal blood oxygenation circuit into an arterial portion of a patient circulation system; measuring the first blood flow rate; establishing a first removal rate of carbon dioxide from the blood in an oxygenator in the extracorporeal circuit; determining (i) at least one of a first arterial carbon dioxide content or a first arterial carbon dioxide content surrogate and (ii) at least one of a first carbon dioxide content or a first carbon dioxide content surrogate in the blood delivered to the patient after passing the oxygenator corresponding to the first removal rate of carbon dioxide from the blood; establishing a second removal rate of carbon dioxide from the blood in the oxygenator in the extracorporeal circuit; determining (i) at least one of a second arterial carbon dioxide content or a second arterial carbon dioxide content surrogate and (ii) at least one of a second carbon dioxide content or a second carbon dioxide content surrogate in the blood delivered to the patient after passing the oxygenator corresponding to the second removal rate of carbon dioxide from the blood; and calculating a cardiac output of the patient corresponding to the first blood flow rate, the at least one of first arterial carbon dioxide content or the first arterial carbon dioxide content surrogate, the at least one of first carbon dioxide content or the first carbon dioxide content surrogate; the at least one of second arterial carbon dioxide content or the second arterial carbon dioxide content surrogate and the at least one of the second carbon dioxide content or the second carbon dioxide content surrogate.

A further alternative method is provided for calculating cardiac output of a patient undergoing veno-arterial extracorporeal blood oxygenation, the method including establishing a first blood flow rate in an extracorporeal blood oxygenation circuit from a venous portion of a patient circulation system into an arterial portion of the patient circulation system; measuring the first blood flow rate; establishing a first exchange rate of a gas with the blood in the extracorporeal blood oxygenation circuit; measuring a first value of a blood parameter in the arterial portion of the patient circulation system corresponding to the first exchange rate; measuring a first value of the blood parameter in the blood delivered to the patient corresponding to the first exchange rate; establishing a second exchange rate of the gas with the blood in the extracorporeal blood oxygenation circuit; measuring a second value of the blood parameter in the arterial portion of the patient circulation system corresponding to the second exchange rate; measuring a second value of the blood parameter in the blood delivered to the patient corresponding to the second exchange rate; and calculating a cardiac output of the patient corresponding to the first blood flow rate and (x) the first value of a blood parameter in an arterial portion of the patient circulation system corresponding to the first exchange rate, (xx) the first value of the blood parameter in the blood delivered to the patient corresponding to the first exchange rate, (y) the second value of the blood parameter in the arterial portion of the patient circulation system corresponding to the second exchange rate and (yy) the second value of the blood parameter in the blood delivered to the patient corresponding to the second exchange rate.

An alternative apparatus for quantifying a cardiac output of a patient operably connected to an extracorporeal blood oxygenation circuit, the extracorporeal blood oxygenation circuit having an access line withdrawing blood from the circulation system of the patient, a blood oxygenator, a pump and a return line returning oxygenated blood to an arterial portion of the circulation system, wherein the apparatus includes a controller configured to connect to one of the blood oxygenator or the pump, the controller configured to calculate a cardiac output of the patient based on a measured first flow rate of oxygenated blood from the extracorporeal circuit, a first arterial carbon dioxide content or surrogate and a first carbon dioxide content or surrogate measured during a first flow rate of sweep gas though an oxygenator in the extracorporeal circuit; and a second arterial carbon dioxide content or surrogate and a second carbon dioxide content or surrogate measured during a second flow rate of sweep gas though the oxygenator in the extracorporeal circuit.

The following will describe embodiments of the present disclosure, but it should be appreciated that the present disclosure is not limited to the described embodiments and various modifications of the invention are possible without departing from the basic principles. The scope of the present disclosure is therefore to be determined solely by the appended claims.

BRIEF DESCRIPTION OF THE SEVERAL VIEWS OF THE DRAWING(S)

DETAILED DESCRIPTION OF THE INVENTION

Figure 1:
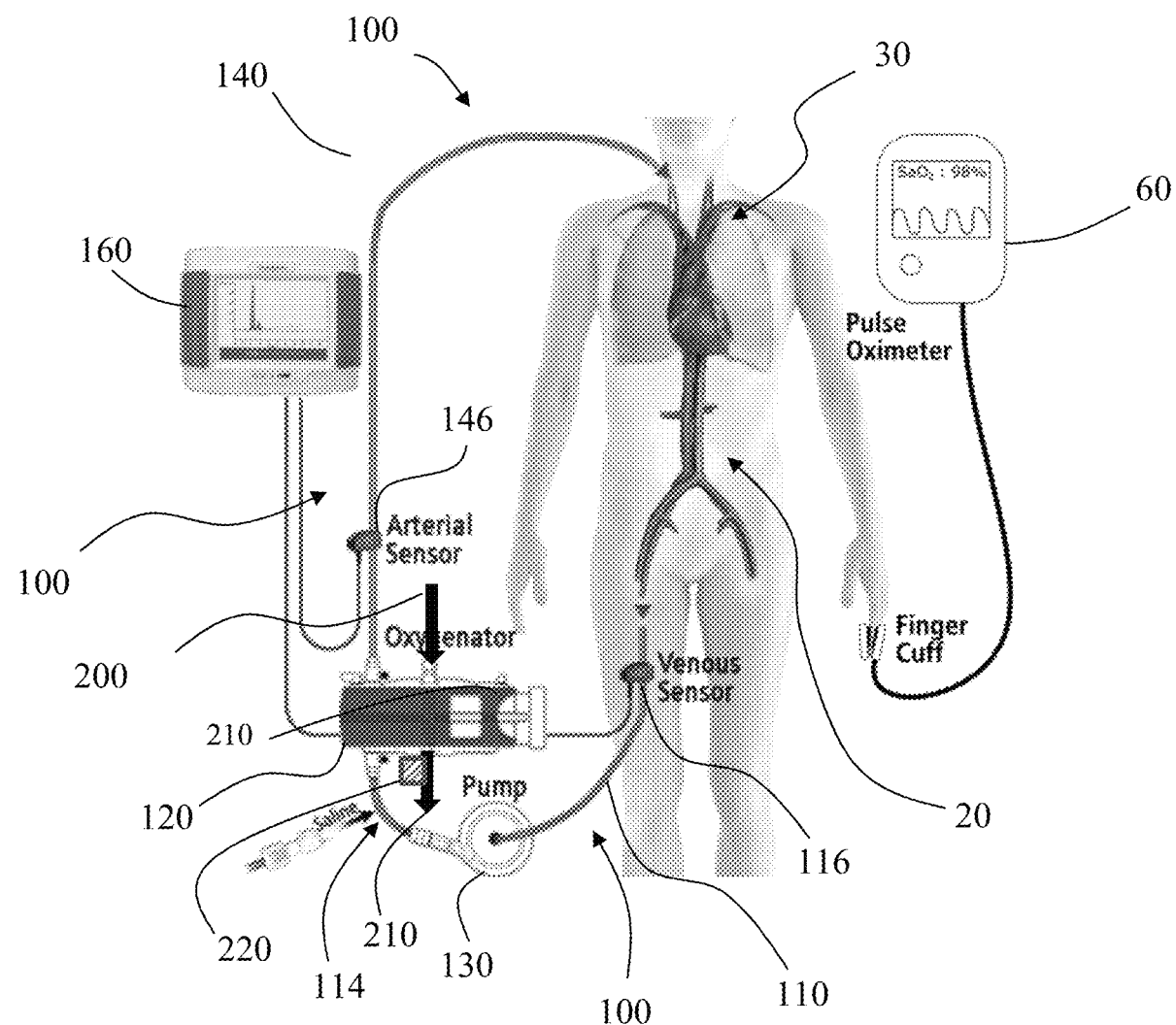
FIG. 1 is a representative veno-arterial extracorporeal blood oxygenation circuit.

Referring to FIG. 1, an extracorporeal blood oxygenation circuit 100 is shown connected to a circulation system 20 of a patient.

The circulation system 20 is a human (or animal) circulatory system including blood, a vascular system, and a heart. For purposes of this description, the circulation system 20 is includes a cardiopulmonary system 30 and a systemic system connecting the cardiopulmonary system 30 to the tissues of the body. Specifically, the systemic system passes the blood though the vascular system (arteries, veins, and capillaries) throughout the body.

The cardiopulmonary system 30 includes the right heart, the lungs and the left heart, as well as the vascular structure connecting the right heart to the lungs, the lungs to the left heart and some portion of the aorta and large veins located between the extracorporeal circuit and the right and left heart. That is, in theory the cardiopulmonary system 30 would include only the right heart, the lungs, the left heart and the vascular structure directly connecting the right heart to the lungs and the lungs to the left heart. However, in practice it is sometimes impracticable to operably connect the extracorporeal circuit 100 immediately adjacent the large vein at the right heart, or immediately adjacent the aorta at the left heart. Therefore, the cardiopulmonary system 30 often includes a limited length of the veins entering the right heart and the aorta exiting the left heart. For example, the extracorporeal circuit 100 can be connected to a femoral artery and femoral vein, thereby effectively extending the cardiopulmonary system 30 to such femoral artery or vein.

For cardiopulmonary and vascular systems, the term "upstream" of a given position refers to a direction against the flow of blood, and the term "downstream" of a given position is the direction of blood flow away from the given position. The "arterial" side or portion is that part in which oxygenated blood flows from the heart to the capillaries. The "venous" side or portion is that part in which blood flows from the capillaries to the heart and lungs (the cardiopulmonary system 30).

The basic components of the extracorporeal circuit (or extracorporeal blood oxygenation circuit) 100 for a conventional extracorporeal oxygenation machine include an access (or venous) line 110, an oxygenator 120 and heat exchanger (not shown), a pump 130, a return (or arterial) line 140, a sensor 116 in the venous line, a sensor 146 in the arterial line and a controller 160. For purposes of description, the access (or venous) line 110 is referred to as the access line and the return (or arterial) line 140 is referred to as the return line.

The extracorporeal circuit 100 is configured to form a veno-arterial (VA) extracorporeal circuit 100. In the veno-arterial extracorporeal circuit 100, the site of the withdrawal of blood from the circulation system 20 to the extracorporeal circuit 100 is a venous portion of the circulation system and the site of introduction of blood from the extracorporeal circuit to the circulation system is an arterial portion of the circulation system as shown in FIGS. 2 and 3.

Figure 2:
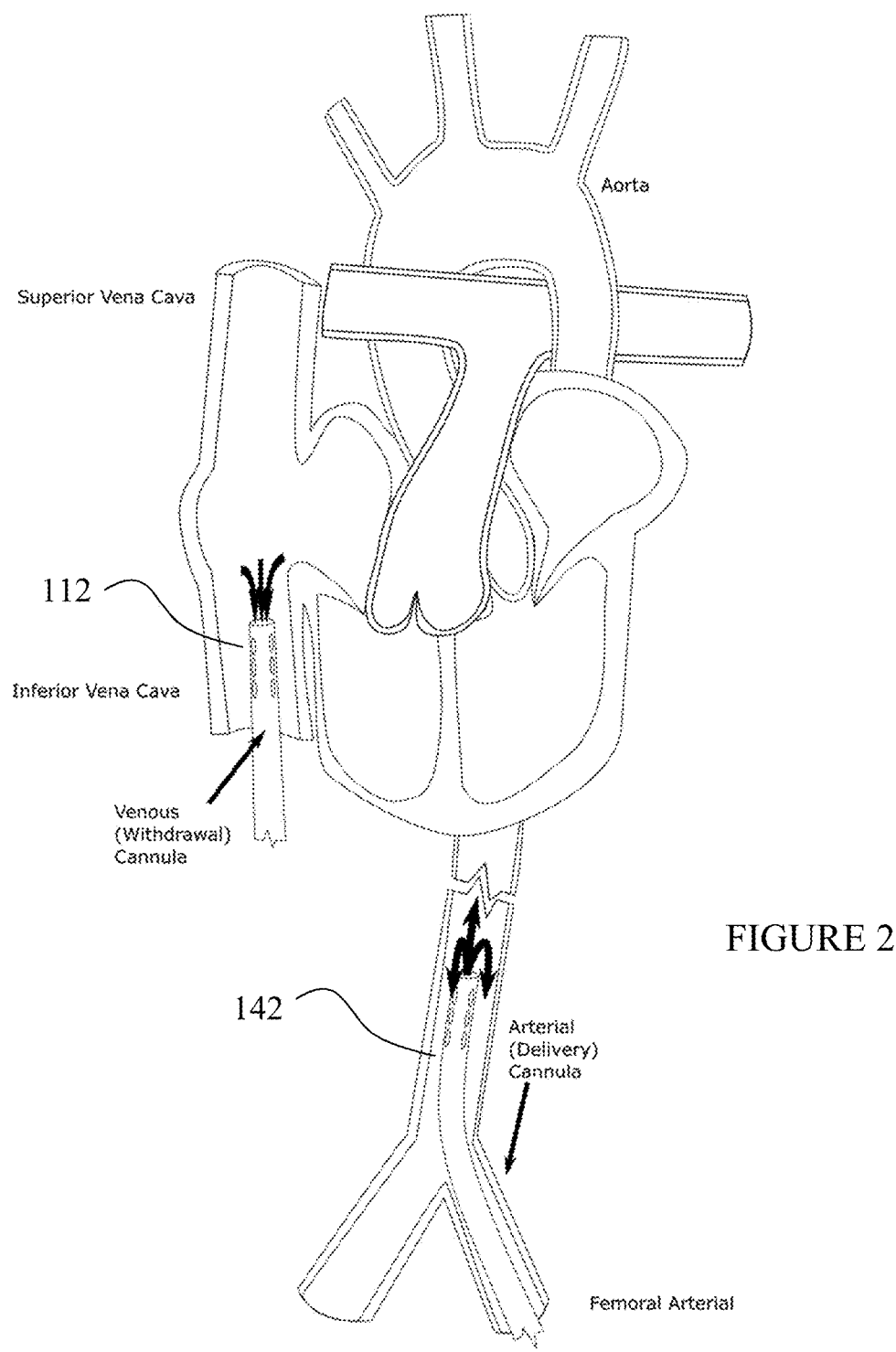
FIG. 2 is representation of a location of blood introduction and blood withdrawal in the veno-arterial extracorporeal blood oxygenation circuit.
Figure 3:
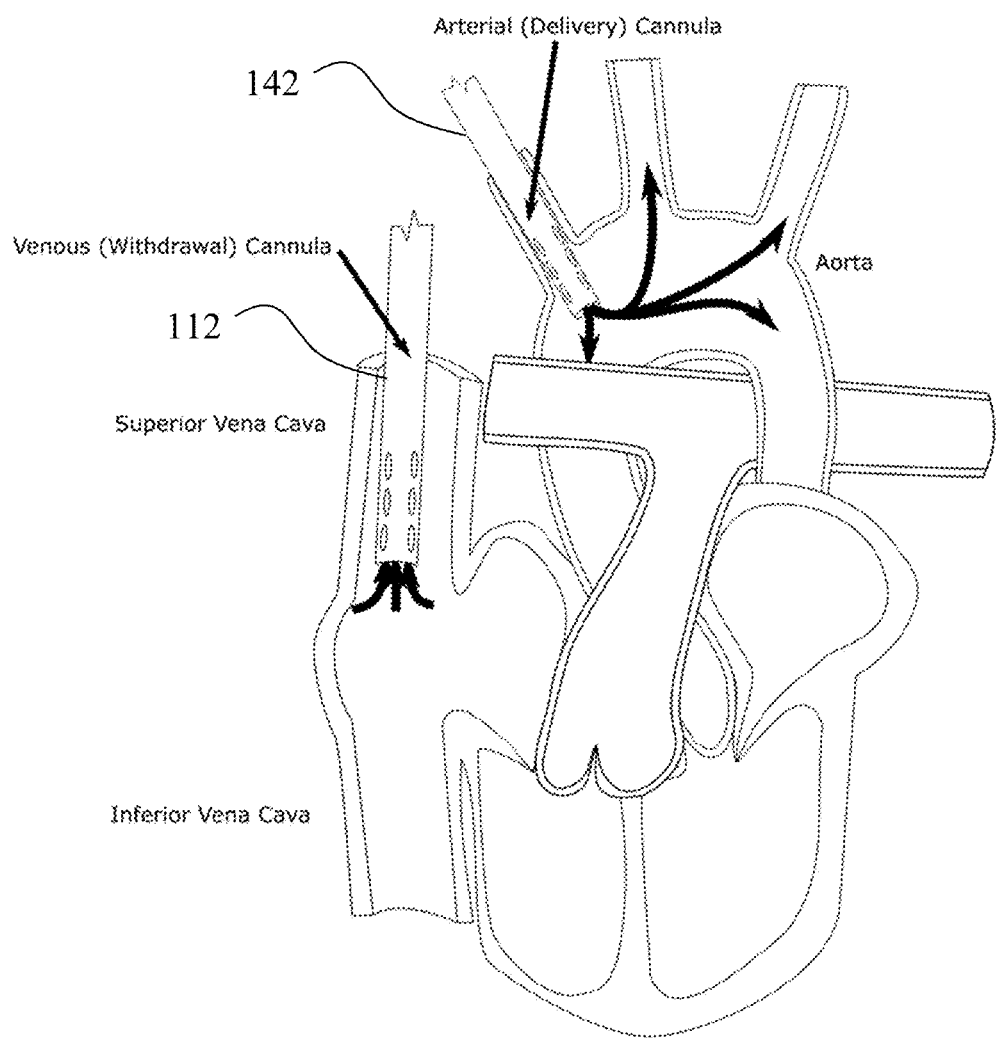
FIG. 3 is representation of an alternative location of blood introduction and blood withdrawal in the veno-arterial extracorporeal blood oxygenation circuit.

As seen in FIGS. 2 and 3, the site of withdrawal of blood from the circulation system 20 to the extracorporeal circuit 100 can include the inferior vena cava, the superior vena cava and/or the right atria and the site of introduction of blood from the extracorporeal circuit to the circulation system can include the aorta, a femoral artery or intermediate arterial vessels.

Thus, the VA extracorporeal circuit 100 withdraws blood from the venous portion of the circulation system 20 (including the cardiopulmonary system 30), and returns the blood to the arterial portion of the circulation system (including the cardiopulmonary system). The withdrawn blood can be treated while it is withdrawn, such as through gas exchange or oxygenation (ECMO) before being returned to the arterial portion of the circulation system 20. The blood treatment can be any of a variety of treatments including, but not limited to, oxygenation (and carbon dioxide withdrawal) or merely circulation (pumping), thereby relieving the load on the heart.

The access line 110 extends from the venous portion of the circulation system 20, and preferably from a venous portion of the cardiopulmonary system 30. Referring to FIGS. 2 and 3, the access line 110 typically includes a venous (or access) cannula 112 providing the fluid connection to the circulation system 20.

Depending upon the configuration of the extracorporeal circuit 110 and the mechanisms for measuring the blood parameters, the access line 110 can also include or provide an indicator introduction port 114 as the site for introducing an indicator into the extracorporeal circuit 100. In one configuration, the indicator introduction port 114 for introducing the dilution indicator is upstream to an inlet of the oxygenator 120. In selected configurations, the introduction site 114 can be integrated into the oxygenator 120.

In the access line 110, the sensor 116, if employed, can be a dilution sensor for sensing passage of the indicator through the extracorporeal circuit 100. The dilution sensor 116 (as well as sensor 146) can be any of a variety of sensors, and can cooperate with the particular indicator. The sensor 116 (as well as sensor 146) can measure different blood properties: such as but not limited to temperature, Doppler frequency, electrical impedance, optical properties, density, ultrasound velocity, concentration of glucose, oxygen saturation and other blood substances (any physical, electrical or chemical blood properties). It is also understood the sensor 116 can also measure the blood flow rate. Alternatively, there can be a sensor (not shown) in addition to sensor 116 be to measure the blood flow rate. Thus, in one configuration the present system includes a single blood property sensor and a single flow rate sensor. It is further contemplated that a single combined sensor for measuring flow rate and a blood parameter (property) can be used. As set forth herein, in some pumps 130, a rotational speed, RPM (rotations per minute) of the pump can be measured for providing a measurement of blood flow rate.

The return line 140 connects the extracorporeal circuit 100 to an arterial portion of the circulation system 20 and in one configuration to an arterial portion of the cardiopulmonary system 30, such as the aorta. Alternatively, the return line 140 can connect to the femoral artery. The return line 140 typically includes a return (arterial) cannula 142 providing the fluid connection to the arterial portion of the circulation system 20.

The return line 140 can also include a sensor such as the sensor 146. The sensor 146 can be any of a variety of sensors, as set forth in the description of the sensor 116, and is typically selected to cooperate with the anticipated indicator. While the system is described with the two sensors 116, 146, for an enhanced accuracy of indicator dilution measurements, it is understood only a single sensor is necessary.

However, it is understood the sensors 116, 146 can be located outside of the extracorporeal circuit 100. That is, the sensors 116, 146 can be remotely located and measure in the extracorporeal circuit 100, the changes produced in the blood from the indicator introduction or values related to the indicator introduction which can be transmitted or transferred by means of diffusion, electro-magnetic or thermal fields or by other means to the location of the sensor.

The oxygenator 120 can be broadly classified into bubble type oxygenators and membrane type oxygenators. The membrane type oxygenators fall under the laminate type, the coil type, and the hollow fiber type. Membrane type oxygenators offer advantages over the bubble type oxygenators as the membrane type oxygenators typically cause less blood damage, such as hemolysis, protein denaturation, and blood coagulation as compared with the bubble type oxygenators. Although the preferred configuration is set forth in terms of a membrane type oxygenator, it is understood any type of oxygenator can be employed.

The pump 130 can be any of a variety of pumps types, including but not limited to a peristaltic or roller (or impeller or centrifugal) pump. The pump 130 induces a blood flow rate through the extracorporeal circuit 100. Depending on the specific configuration, the pump 130 can be directly controlled at the pump or can be controlled through the controller 160 to establish a given blood flow rate in the extracorporeal circuit. The pump 130 can be at any of a variety of locations in the extracorporeal circuit 100, and is not limited to the position shown in the Figures. In one configuration, the pump 130 is a commercially available pump and can be set or adjusted to provide any of a variety of flow rates wherein the flow rate can be read by a user and/or transmitted to and read by the controller 160.

The controller 160 is typically connectable to the oxygenator 120, the pump 130 and the sensor(s) 116, 146 if employed. The controller 160 can be a stand-alone device such as a personal computer, a dedicated device or embedded in one of the components, such as the pump 130 or the oxygenator 120. Although the controller 160 is shown as connected to the sensors 116 and 146, the pump 130 and the oxygenator 120, it is understood the controller can be connected to only the sensors, the sensors and the pump, or any combination of the sensors, pump and oxygenator. In one configuration, at least one of the pump 130 and the controller 160 provides for control of the pump and the flow rate of the blood through the pump, respectively. It is also understood, the controller 160 also can be connected to an oximeter 60, such as a pulse oximeter, to automatically collect data or oximetry data can be put manually into controller. Alternatively, the oximeter 60 and the controller 160 can be integrated as a single unit.

The controller 160 is programmed with the equations as set forth herein and can perform the associated calculations based on inputs from the user or connected components.

The normal or forward blood flow through the extracorporeal circuit 100 includes withdrawing blood through the access line 110 from the venous side circulation system 20 (and particularly the venous portion of the cardiopulmonary circuit 30), passing the withdrawn blood through the extracorporeal circuit (to treat such as oxygenate), and introducing the withdrawn (or treated or oxygenated or circulated) blood through the return line 140 into the arterial side of the circulation system. The pump 130 thereby induces a blood flow at a known (measured) blood flow rate through the extracorporeal circuit 100 from the access line 110 to the return line 140.

For purposes of the present description, the following terminology is used. Cardiac output CO is the amount of blood pumped out by the left ventricle in a given period of time (typically a 1 minute interval). The heart capacity (flow) is typically measured by cardiac output CO. The term blood flow rate means a rate of blood passage, volume per unit time. The blood flow rate is a volumetric flow rate ("flow rate"). The volumetric flow rate is a measure of a volume of liquid passing a cross-sectional area of a conduit per unit time, and may be expressed in units such as milliliters per min (ml/min) or liters per minute (l/min).

The current disclosure provides a simple noninvasive technology to measure CO in VA extracorporeal blood oxygenation, such as a VA ECMO setting. To apply the present technique to measure cardiac output CO during VA extracorporeal blood circulation, including oxygenation, such as ECMO, the following terms are employed:

$SvO_2$—mixed venous saturation of blood that did not pass through the oxygenator 120

$SaO_2$—arterial saturation, (which as set forth below can be measured by blood sample or by oximetry, including pulse oximetry)

$Q_b$—extracorporeal flow rate, (which as set forth below can be measured by a flow rate of the pump 130 in the extracorporeal circuit 100)

CO—Cardiac output

Balance Equation

In the first instance, a mass balance equation is applied to the extracorporeal circuit 100. For this analysis, the following assumptions are made:

1. Oxygenation of the blood passing through the lungs is small (negligible).
2. Oxygen saturation of the blood after oxygenator is at or near 100%. (The formula below can be adjusted for a different value of oxygen saturation from the oxygenator.)

With the appropriate accounting for oxygen, an initial equation becomes:

$$Q_b*100+CO*SvO_2=(CO+Qb)*SaO_2 \qquad \text{Eq. 1}$$

Solving for CO:

$$Q_b*100 + CO*SvO_2 - Q_b*SaO_2 = CO*SaO_2 \qquad \text{Eq. 2}$$

$$CO \times (SaO_2 - SvO_2) = Qb \times (100 - SaO_2) \qquad \text{Eq. 3}$$

$$CO = Q_b \times \frac{(100 - SaO_2)}{(SaO_2 - SvO_2)} \qquad \text{Eq. 4}$$

Currently, during VA ECMO treatment, $Q_b$ and $SaO_2$ are routinely measured, while $SvO_2$ is difficult to measure. That is, the value of venous saturation measured pre-oxygenator in extracorporeal (ECMO) circuit 100 may be different from mixed venous saturation in the cardiopulmonary system 30.

Theoretically in equation 4, $SvO_2$ should be equal to saturation of blood coming from the lungs, thus providing a potential surrogate. If lungs are not working, this assumption that $SvO_2$ is close saturation in the lungs is accurate. However, in the case that the lungs are partly working, then substituting saturation after the lungs by $SvO_2$ will increase errors in the calculation of CO.

Therefore, Equation 4 can be used with the measured and reliable values of Qb and $SaO_2$ in conjunction with a measured $SvO_2$, such as measured in the access line 110, recognizing the measured surrogate value of $SvO_2$ value may introduce an unacceptable error.

Thus, depending on the confidence in the $SvO_2$ value, there are 2 unknowns in Equation 4, so the equation can still be used for CO calculation (assessment), but is less accurate.

Two Balance Equations

To increase the accuracy of the CO measurement by eliminating the potentially unreliable or unknown value of $SvO_2$, the value of $Q_b$ (such as via flow rate of the pump 130 in the extracorporeal circuit 100) can be changed, such as by an increase or decrease to deliver a different flow rate of 100% oxygenated blood through the return line 140 and into the arterial portion of the circulation system 20, such as the aorta. In one configuration, the amount of change in the pump flow rate and the corresponding change in the measured parameters is outside of normal operating variances, operating error or drift.

For purposes of description, it is assumed the flow rate of oxygenated blood from the oxygenator 120 is decreased, such as by decreasing pump flow rate (where $Q_{b(2)} < Q_{b(1)}$). Thus, less 100% oxygenated blood is delivered from the extracorporeal circuit 100 and measured on the arterial side of the patient, $SaO_{2(2)} < SaO_{2(1)}$. From this difference, a change in $SaO_2$, $\Delta SaO_2$, can be written as:

$$\Delta SaO_2 = SaO_{2(1)} - SaO_{2(2)} \qquad \text{Eq. 5}$$

where index "(1)" and "(2)" correspond to a first flow rate delivered by the extracorporeal circuit 100, such as a first pump setting, $Q_{b(1)}$ and a second flow rate delivered by the extracorporeal circuit, such as a second pump setting pump setting $Q_{b(2)}$, respectively.

For this application of two balance equations analogous to Eq. 4, it is assumed the value of CO between the two flow rates through the extracorporeal circuit 100 does not change or that any actual change is insubstantial or negligible. Thus, the two equations for the two different flow rates of oxygenated blood from the extracorporeal circuit 100 are:

$$CO = Q_{b(1)} \times \frac{(100 - SaO_{2(1)})}{(SaO_{2(1)} - SvO_{2(1)})} \qquad \text{Eq. 6}$$

$$CO = Q_{b(2)} \times \frac{(100 - SaO_{2(2)})}{(SaO_{2(2)} - SvO_{2(2)})} \qquad \text{Eq. 7}$$

During the decrease in $SaO_2$ from $SaO_{2(1)}$ to $SaO_{2(2)}$, a decrease of $SvO_2$ is also expected. However, the magnitude of this decrease in $SvO_2$ is unknown. If the magnitude of the decrease in $SaO_2$ is small, then the assumption is made that $SvO_{2(1)} \approx SvO_{2(2)}$, then the system of equations (Eq. 6 and Eq. 7) with 2 unknowns (CO and $SvO_2$) can be solved for CO, which in turn can then be calculated from the known or measured $Q_{b(1)}$, $Q_{b(2)}$, and $SaO_{2(1)}$ and $SaO_{2(2)}$, without relying upon a value of $SvO_2$.

However, it is also understood that a decrease of pump flow rate $Q_{b(1)}$ to $Q_{b(2)}$ may lead to the situation that more blood will be available (more preload) to the heart and the cardiac output (CO) may actually increase, and can increase up to the amount of the pump flow rate decrease. So for a cardiac output for the first pump flow rate $CO_{(1)}$ and the increased cardiac output $CO_{(2)}$ during the decreased pump flow rate, the following applies.

$$CO_{(2)} - CO_{(1)} = Q_{b(1)} - Q_{b(2)} \qquad \text{Eq. 8}$$

Thus Equations 6 and 7 become:

$$CO_{(1)} = Q_{b(1)} \times \frac{(100 - SaO_{2(1)})}{(SaO_{2(1)} - SvO_{2(1)})} \qquad \text{Eq. 6A}$$

$$CO_2 = Q_{b(2)} \times \frac{(100 - SaO_{2(2)})}{(SaO_{2(2)} - SvO_{2(2)})} \qquad \text{Eq. 7A}$$

and consider Eq.8

$$CO_{(1)} = Q_{b(1)} \times \frac{(100 - SaO_{2(1)})}{(SaO_{2(1)} - SvO_{2(1)})} \qquad \text{Eq. 6B}$$

$$CO_{(1)} + (Q_{b(1)} - Q_{b(2)}) = Q_{b(2)} \times \frac{(100 - SaO_{2(2)})}{(SaO_{2(2)} - SvO_{2(2)})} \qquad \text{Eq. 7B}$$

In the event that $SvO_{2(1)} \approx SvO_{2(2)}$, then Equations 6B and 7B having two unknowns, $CO_{(1)}$ and $SvO_{2(1)}$ (which equals or approximates $SvO_{2(2)}$) can be solved. These can be used for the value of CO can be equal or between $CO_{(2)}$ and $CO_{(1)}$.

If the decrease of $SvO_{2(1)}$ is a portion or fraction of the decrease of the arterial saturation, $\Delta SaO_2$, (Eq. 5), then the value $SvO_{2(2)} = SvO_{2(1)} - K \ast \Delta SaO_2$: where K is for example 0.5 (but could be 0.1, 0.2 or 0.7 (or whatever the appropriate factor), can be used in Equations 7A and 7B where the value $SvO_{2(2)}$ will be substituted and again, a system of two equations with two unknowns (CO and $SvO_2$) or ($CO_{(1)}$ and $SvO_2$) is provided, wherein the equations can be solved to determine CO ($CO_{(1)}$), without requiring a value or measurement of $SvO_2$.

Analogously, if the increase of $CO_{(1)}$ is a portion or fraction of the decrease of the pump flow, $Q_{b(1)} - Q_{b(2)}$, (Eq. 8), then the value $CO_{(2)} = CO_{(1)} + R \ast (Q_{b(1)} - Q_{b(2)})$: where R is for example 0.5 (but could be 0.1, 0.2 or 0.7 (or whatever the appropriate factor), can be used in Equations 7A and 7B where the value $CO_{(2)}$ will be substituted and again, a system of two equations with two unknowns (CO and $SvO_2$) or ($CO_{(1)}$ and $SvO_{2(1)}$) is provided, wherein the equations can be solved to determine CO ($CO_{(1)}$).

Theoretically, it is believed the actual CO will be between the value calculated from Equations 6 and 7 and the value calculated from Equations 6B and 7B. Practically, it is observed that after the decrease of arterial oxygen saturation, the venous oxygen saturation also decreases.

It is believed in case of the lungs partly working (thereby partly oxygenating the blood) the actual mass balance equations need to include an after-lung situation instead of venous situations. The benefit of the current two flow rate concept is that it is independent of (eliminates) the need for assumptions of venous oxygen saturations in Eq. 4 as used for a surrogate of mix venous oxygen saturation. In addition, there may be intermediate conditions (assumptions) applied to Equations 6 and 7 and Equations 6A and 7A, like the assumption that $SvO_{2(2)}$ does not decrease the entire amount of decrease in $SaO_2$ as per $\Delta SaO_2$, but on a portion such as ⅓ or ⅕ etc., then all the solutions for the CO value will be in-between calculation from Equations 6 and 7 and the calculation from Equations 6A and 7A.

Although Equations 6 and 7 as well as 6A and 7A, and 6b and 7B are based on two different flow rates from the extracorporeal circuit 100 (and the corresponding measurements), it is believed that three, four or more blood flow rates can be established, and the measurements used to further calculate the cardiac output, CO, by merely employing additional iterations of these equations. Thus, in certain configurations there is at least one change in the flow rate from the extracorporeal circuit 100, although there can be two, three or more flow rate changes (and corresponding measured parameters).

In application, the CO of the patient on extracorporeal blood oxygenation, such as VA-ECMO can be obtained in the following configurations.

In one configuration, the patient, and particularly the circulation system 20, is operably connected to the extracorporeal circuit 100, wherein the access line 110, which can include the access cannula as known in the art, withdraws blood from the patient, and particularly a venous portion of the circulation system 20 and in one configuration from the vena cava or the right atria.

The withdrawn blood is passed through the access line 110 through the pump 130 and to the oxygenator 120. The blood is oxygenated in the oxygenator 120 and then pumped through the return line 140 for introduction to the patient, and particularly the arterial portion of the circulation system 20 and more particularly into the aorta or femoral artery.

To calculate the CO, the amount of oxygenated blood introduced into the circulation system 20 is measured, such as by reading the setting of the pump 130. However, it is understood alternatively mechanisms can be used to measure the flow of oxygenated blood, such as by not limited to flow meters in the extracorporeal circuit 100, dilution measurements or ultrasonic measurements as known in the art.

The arterial oxygen saturation, $SaO_2$, is measured such as by pulse oximetry with the oximeter 60 or arterial blood gas analysis. As seen in FIG. 1, the pulse oximeter 60 is connected to the patient to measure arterial oxygen saturation, $SaO_2$.

The venous oxygen saturation, $SvO_2$, is measured at the inlet of the oxygenator 120 in the extracorporeal circuit 100. It is understood this measurement is not of mixed venous oxygenation saturation, and not the blood coming from the lungs, but is rather a surrogate. However, in view of the invasive nature and potential complications inherent in drawing blood from the pulmonary artery or after the lungs, the measurement of oxygen saturation from the blood drawn from the inferior vena cava or right atria is used.

It is understood, the method for calculating CO is not limited to the manner of measurement of the parameter upon which the CO is measured.

Then assuming no or negligible lung function and the right atria venous saturation is close to (or approximates) the mixed venous saturation, then CO is calculated by:

$$CO = Q_b \times \frac{(100 - SvO_2)}{(SaO_2 - SvO_2)} \quad \text{Eq. 4}$$

$SaO_2$=saturation of arterial blood
$SvO_2$=saturation of venous blood withdrawn from the patient from the right atrium or from the vena cava.

In an alternative configuration employing select equations from above, the patient is operably connected to the extracorporeal circuit 100 as set forth above. It is further understood that although the present method is set forth with specific manner of obtaining measurements, any available manner of obtaining the identified data can be employed.

In this alternative configuration, the amount of oxygenated blood introduced into the patient circulation system 20 is measured (or identified such as by the setting of the pump 130). The arterial oxygen saturation, $SaO_2$, is then measured by the oximeter 60, such as set forth above.

The flow rate of oxygenated blood from the extracorporeal circuit 100 and introduced to the circulation system 20 is then changed by an amount sufficient to generate a corresponding change to $SaO_2$. In one configuration, the amount of change is outside of normal operating variances, operating error or drift, produces a change in $SaO_2$ that is also outside of normal operating variances, operating error and drift, thereby producing a change the reasonably attributable to the intentionally imparted change in the flow rate and resulting change in parameters. Specifically, in one configuration the amount of change in the flow rate of oxygenated blood from the extracorporeal circuit 100 is sufficient to impart a change in the measured $SaO_2$ that is greater than operating error, drift or variance. In some configurations, the change in flow rate of oxygenated blood from the extracorporeal circuit 100 is at least 10% of the original flow rate, and in further configurations at least 20% of the original flow rate, an in other configurations at least 30% of the original flow rate. It is understood the change in flow rate of oxygenated blood from the extracorporeal circuit 100 can be varied depending on the particular set of circumstances, without deviating from the present system.

The change in the flow rate of oxygenated blood from the extracorporeal circuit 100 to the circulation system 20 can be readily imparted by changing the operation of the pump 130. Thus, the second flow rate of oxygenated blood is introduced into the circulation system 20.

After changing the oxygenated blood flow rate of the extracorporeal circuit 100, approximately 1 minute to 2 minutes can elapse before measuring, by the oximeter 60, the arterial oxygen saturation $SaO_2$, for the second flow rate. That is, the arterial oxygen saturation, $SaO_2$, is measured, such as set forth above during the second flow rate of oxygenated blood passing into the circulation system 20.

The different second flow rate of oxygenated blood imposed in the extracorporeal circuit 100 is sufficient to impart a change in at least the arterial oxygen saturation, $SaO_2$ that is outside operating variances, operating error or drift, such as set forth above.

Of note, there is no need for a measurement of $SvO_2$ or a surrogate parameter in this configuration. The CO can then be calculated through Equations 6 and 7 and Equations 6A and 7A from the measured first and second flow rate of oxygenated blood introduced into the circulation system 20, and the corresponding arterial oxygen saturation, $SaO_2$ for each flow rate.

If indicator dilution techniques are used, it is understood the indicator is any substance that alters a measurable blood property. The indicator may alter any measurable parameter of the blood. For example, the indicator may be chemical, optical, electrical, thermal or any combination thereof. The particular indicator is at least partly dictated by the anticipated operating environment. Available indicators include saline solutions, increased or decreased temperature as well as dyes and various isotopes. The use of temperature differentials may be accomplished by locally creating a heat source (such as a heater in the oxygenator 120) or a heat sink in the surrounding flow. The creation of a local temperature gradient offers the benefit of being able to employ a dilution indicator without introducing any additional volume into the blood flow. That is, a temperature differential may be created without an accompanying introduction of a volume of indicator. Alternatively, a volume of heated or cooled blood may be introduced at the indicator introduction port 114 as the indicator. It is also contemplated, that a component of the extracorporeal circuit 100 can be controlled to create or induce an indicator within the flow in the extracorporeal circuit. For example, a filtration or treatment rate or heater (chiller) can be sufficiently changed to create an effective indicator in the extracorporeal circuit 100 which then travels through the cardiopulmonary system 30.

In a further configuration, a change is a gas exchange between the blood passing the extracorporeal blood oxygenation circuit 100 and the oxygenator 120 is imparted over a constant flow rate in the extracorporeal blood oxygenation circuit and a mass balance is applied to calculate the cardiac output. In a specific configuration, a carbon dioxide balance is applied across a change in carbon dioxide in the blood rather than a change of a blood parameter corresponding to a change in the flow rate Qb in the extracorporeal circuit 100.

The purpose of the present system is to provide a simple noninvasive technology to measure CO in VA extracorporeal blood oxygenation, such as in a VA ECMO setting. To apply the present technique to measure cardiac output CO during VA extracorporeal blood oxygenation, including ECMO, the following terms are employed.

$S_1CO_2$—carbon dioxide content leaving lungs coming to the aorta and can be measured/estimated by capnography of expired air.

$S_aCO_2$—arterial carbon dioxide content, (which as set forth below can be measured by arterial blood sample (arterial blood gas analysis) or estimated via the surrogate, including but not limited to arterialized capillary blood gas analysis; or partial pressure of transcutaneous carbon dioxide.

$S_{ecmo}CO_2$—carbon dioxide content in the blood delivered to the patient after passing the oxygenator 120, which as set forth herein can be directly measured from the blood passing to the patient or determined or calculated via a surrogate like carbon dioxide partial pressure measured by the sensors in the outflow of sweep gas air from the oxygenator.

$Q_b$—extracorporeal flow rate, (which as set forth herein can be measured by a flow rate of the pump 130 in the extracorporeal circuit 100 or readily measured with commercially available flow meters).

CO—Cardiac output.

For purposes of this analysis, it is assumed that the carbon dioxide content in the blood, ($SCO_2$) leaving the oxygenator 120 through the outlet 210 ($S_{ecmo}CO_2$) is not materially affected by $Q_b$, but rather predominantly determined by the sweep gas flow rate in the oxygenator 120.

The value of carbon dioxide content in the blood, $S_{ecmo}CO_2$, can be measured by direct blood sampling (arterial blood gas analysis) or estimated via a surrogate or by a sensor of carbon dioxide partial pressure in the outflow air (210) from the oxygenator 120. Any of the commercially available sensors for measuring the actual carbon dioxide partial pressure, or surrogate value like carbon dioxide partial pressure, can be used for this measurement.

The surrogate is a value that is related to $SCO_2$ content which includes but is not limited to: the partial pressure of $CO_2$ in the gas, the partial pressure of $CO_2$ dissolved in solution, the bicarbonate concentration of blood, and carbaminohemoglobin concentration. In general, it is assumed that use of a surrogate rather than the true content may be less accurate. It is understood that measuring a surrogate parameter or using a surrogate parameter is encompassed within measuring the named parameter.

Balance Equation

A mass balance equation for $CO_2$ content in blood can be written for VA ECMO as follows:

$$Q_b \times S_{ecmo}CO_2 + CO \times S_lCO_2 = (CO+Q_b) \times S_aCO_2 \qquad \text{Eq. 9}$$

Where $S_{ecmo}CO_2$ is the $CO_2$ (carbon dioxide) content in blood flowing out of the ECMO extracorporeal circuit 100; $S_lCO_2$ is the $CO_2$ the in blood leaving the lungs and $S_aCO_2$ is the $CO_2$ in the arterial blood.

Solving Eq. 9 for CO:

$$Q_b \times S_{ecmo}CO_2 + CO \times S_lCO_2 = CO \times S_aCO_2 + Q_b \times S_aCO_2 \qquad \text{Eq. 10}$$

$$CO \times (S_aCO_2 - S_lCO_2) = Qb \times (S_{ecmo}CO_2 - S_aCO_2) \qquad \text{Eq. 11}$$

$$CO = Q_b \times \frac{(S_{ecmo}CO_2 - S_aCO_2)}{(S_aCO_2 - S_lCO_2)} \qquad \text{Eq. 12}$$

Currently, during VA ECMO treatment, $Q_b$ and $S_{ecmo}CO_2$ and $S_aCO_2$ can be measured or estimated, while $S_lCO_2$ is difficult to measure accurately from the expired air. Thus, depending on the confidence in the $S_lCO_2$ value, there is one unknown CO in Equation 12, the equation can still be used for CO assessment based on the present terms, but is less accurate.

Two Balance Equations

To increase the accuracy of the CO measurement with the purpose of the elimination of the potentially unreliable or unknown value of $S_lCO2$, and lung influence, the flow rate of the sweep gas through the oxygenator 120 can be changed, thus producing a different value of $S_{ecmo}CO_2$ which will change the arterial content of carbon dioxide, $S_aCO_2$.

An increase in the flow rate of the sweep gas (such as via the sweep gas flow rate of the oxygenator 120 and through the outlet 210) will decrease $S_{ecmo}CO_2$, and a decrease of the sweep gas flow rate increases $S_{ecmo}CO_2$.

Thus, two equations can be produced analogous to Eq. 12 for two different sweep gas flow rates. In the two equation system (one equation for each sweep gas flow rate), index (1) and index (2) represent the first and second sweep gas flow rate, respectively. Upon the assumption that the changes in the $S_lCO_2$ and CO are negligible between the two different sweep gas flow rates, then:

$$CO = Q_b \times \frac{(S_{ecmo}CO_{2(1)} - S_aCO_{2(1)})}{(S_aCO_{2(1)} - S_lCO_{2(1)})} \qquad \text{Eq. 13}$$

$$CO = Q_b \times \frac{(S_{ecmo}CO_{2(2)} - S_aCO_{2(2)})}{(S_aCO_{2(2)} - S_lCO_{2(2)})} \qquad \text{Eq. 14}$$

Considering if $S_lCO_{2(1)}=S_lCO_{2(2)}$, then the system of Equations 13 and 14 has two unknowns CO and $S_lCO_{2(1)}=S_lCO_{2(2)}$, and thus can be solved for CO:

$$CO = Q_b \times \left[\frac{(S_{ecmo}CO_{2(1)} - S_{ecmo}CO_{2(2)})}{(S_aCO_{2(1)} - S_aCO_{2(2)})} - 1\right] \qquad \text{Eq. 15}$$

From Equation 15, it can be seen that cardiac output, CO, can be measured from a known or measured single extracorporeal flow rate $Q_b$, in conjunction with a change in the sweep gas flow rate that provides a corresponding measured change in the (i) arterial carbon dioxide content, $S_aCO_2$, which can be measured by arterial blood sample (arterial blood gas analysis) or estimated via a surrogate using arterialized capillary blood gas analysis, partial pressure of transcutaneous carbon dioxide or other methods; and (ii) the carbon dioxide content in the blood delivered to the patient after passing the oxygenator 120, $S_{ecmo}CO_2$, (which can be calculated or derived or from blood sample in blood delivered to patient from the ECMO extracorporeal circuit 100 or estimated via a surrogate like for example, carbon dioxide partial pressure or from measurements of sensors in the outflow of sweep gas air from the oxygenator 120 for each flow rate).

In one configuration, the change in the measured carbon dioxide contents of Eq. 15 is greater than a nominal operating drift or variance. Typically, this magnitude of change results from a magnitude of change in the flow rate of the sweep gas in the oxygenator 120 that is greater than normal drift or variance during operation of the oxygenator.

If the decrease of $S_lCO_{2(1)}$ is a portion or fraction of the decrease of the arterial carbon dioxide content, $\Delta SaCO_2$, (Eq. 13), then the value $S_lCO_{2(2)}=S_lCO_{2(1)}-K*\Delta SaCO_2$: where K is for example 0.5 (but could be 0.1, 0.2 or 0.7 (or whatever the appropriate factor)), then in Equations 13 and 14 the value $S_lCO_{2(2)}$ will be substituted and again, a system of two equations with two unknowns (CO and $S_lCO_2$) or ($CO_1$ and $S_lCO_{2(1)}$) is provided, wherein the equations can be solved to determine CO ($CO_1$).

Further, while the change in the sweep gas has been set forth as providing the change in carbon dioxide removal, it is understood that any parameter control that imparts a corresponding change of carbon dioxide or another gas or another blood property can be used to measure CO in analogous manner (in place of a specific change in the sweep gas).

Thus, in one configuration, the system includes the controller 160 operably connected to a carbon dioxide sensor 220 in the outflow of sweep gas from the oxygenator 120 from which $S_{ecmo}CO_2$, is measured (or calculated). However, it is understood $S_{ecmo}CO_2$ can also be measured by blood sample from the arterial line. The controller 160 is also connected to a sensor or surrogate (such as an exhaled blood gas analysis or known capnometry) for determining the carbon dioxide content $S_1CO_2$.

The controller 160 is programmed with or has access to a memory with lookup tables for converting a surrogate measurement to the respective carbon dioxide content as set forth above. In addition, the controller 160 is also connected to the pump 130, or a flow meter (not shown) for obtaining the flow rate through the extracorporeal circuit 100. The controller 160 is programmed with the present equations, or equivalents, for calculation of the cardiac output CO.

For purposes of description, the term calculate (or calculating) means determine the amount or number of something mathematically using mathematics, a mathematical processes or equations, as well as evaluate or estimate the nature, amount or quantity. Calculate or calculating means to discover or identify a number or an amount.

For purposes of description, the term measure (or measuring) means how much there is of the relative parameter, including ascertain the size, amount, or degree of (something) such as by using an instrument or device marked in standard units or by comparing it with an object of known size, wherein the measuring may apply to a surrogate value or surrogate parameter. For example, for measuring the oxygenated blood flow rate introduced into the patient circulation system 20, the setting of the pump 130 can be used, a separate flow meter can be used, dilution measurement can be used. It is further contemplated that measuring can include a calculating step or steps.

As used herein, the term surrogate is a parameter which is used as a metric for one or more other parameters. Therefore, for purposes of description, when a specific parameter is recited as measured, it is understood that such measurement includes a representative of the parameter or a surrogate parameter that is measured, without deviating from the present system. Thus, it is understood that measuring a blood flow, recirculation or oxygen saturation encompasses measuring the relevant representative parameter as well as measuring a surrogate parameter. For example, it is understood the oxygen content (which may include contribution from other portions of the blood such as the plasma) can be measured in place of arterial oxygen saturation. Although the present analysis is set forth in terms of oxygen saturation, it is intended that oxygen content can be employed and that the recited oxygen saturation encompasses oxygen saturation as well as oxygen content. Thus, it is understood that measuring a blood flow rate, and/or oxygen saturation includes measuring the relevant parameter or measuring a surrogate parameter.

Although the present method and equations are set forth in terms of oxygen saturation, it is understood that other parameters and/or gases of the blood can be used in place of the blood oxygen saturation. That is, as soon as blood is pumped by the pump 130 in the extracorporeal circuit 100, there will be different physical/chemical property of the blood than the blood flowing in the veins. For example, if the blood is cooled (or heated) in the oxygenator 120, while the blood temperate flowing in the body is at body temperature, then upon measuring the temperature in the artery, the recorded temperature will be a mixture and the analogous concept of heat balance can be applied. As used herein, the term surrogate is a parameter which is used as a metric for one or more other parameters. Therefore, for purposes of description, when a specific parameter is recited as measured, it is understood that such measurement includes a representative of the parameter or a surrogate parameter that is measured, without deviating from the present system. Thus, it is understood that measuring a blood flow, recirculation or oxygen saturation encompasses measuring the relevant representative parameter as well as measuring a surrogate parameter.

It is further contemplated that if the patient were also on a ventilator, a rate of respiration could be changed (decreased or even temporarily halted) to impart a change in a blood parameter to be measured.

Thus, in one configuration the present system includes providing at least a first and a different second flow rate from the extracorporeal circuit 100 wherein a blood parameter is measured on the arterial side of the patient circulation system during or corresponding to the first flow rate and the second flow rate. As set forth above in the equations, these values can then be used to calculate cardiac output.

This disclosure has been described in detail with particular reference to an embodiment, but it will be understood that variations and modifications can be effected within the spirit and scope of the disclosure. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A method for calculating cardiac output of a patient undergoing veno-arterial extracorporeal blood oxygenation, the method comprising:
   (a) establishing a first blood flow rate from an extracorporeal blood oxygenation circuit into an arterial portion of a patient circulation system;
   (b) measuring the first blood flow rate;
   (c) establishing a first removal rate of carbon dioxide from the blood in an oxygenator in the extracorporeal circuit;
   (d) determining (i) at least one of a first arterial carbon dioxide content or a first arterial carbon dioxide content surrogate and (ii) at least one of a first carbon dioxide content or a first carbon dioxide content surrogate in the blood delivered to the patient after passing the oxygenator corresponding to the first removal rate of carbon dioxide from the blood;
   (e) establishing a second removal rate of carbon dioxide from the blood in the oxygenator in the extracorporeal circuit;
   (f) determining (i) at least one of a second arterial carbon dioxide content or a second arterial carbon dioxide content surrogate and (ii) at least one of a second carbon dioxide content or a second carbon dioxide content surrogate in the blood delivered to the patient after passing the oxygenator corresponding to the second removal rate of carbon dioxide from the blood; and
   (g) calculating a cardiac output of the patient corresponding to the first blood flow rate, the at least one of first arterial carbon dioxide content or the first arterial carbon dioxide content surrogate, the at least one of first carbon dioxide content or the first carbon dioxide content surrogate; the at least one of second arterial carbon dioxide content or the second arterial carbon dioxide content surrogate and the at least one of the second carbon dioxide content or the second carbon dioxide content surrogate.

2. The method of claim 1, wherein establishing a first removal rate of carbon dioxide from the blood in an oxygenator in the extracorporeal blood oxygenation circuit includes establishing a first sweep gas flow rate through the oxygenator.

3. The method of claim 1, wherein the second removal rate of carbon dioxide from the blood in the oxygenator in the extracorporeal circuit differs from the first removal rate of carbon dioxide from the blood in the oxygenator in the extracorporeal circuit by an amount greater than normal operating variation.

4. The method of claim 1, wherein measuring the first blood flow rate is provided by a pump in the extracorporeal blood oxygenation circuit.

5. The method of claim 1, wherein establishing the first removal rate of carbon dioxide from the blood in the oxygenator in the extracorporeal circuit and establishing the second removal rate of carbon dioxide from the blood in an oxygenator in the extracorporeal circuit occur during the first blood flow rate.

6. The method of claim 1, wherein measuring the first arterial carbon dioxide content includes measuring a first arterial carbon dioxide content surrogate parameter.

7. The method of claim 1, wherein measuring the second arterial carbon dioxide content includes measuring a second arterial carbon dioxide content surrogate parameter.

8. The method of claim 1, wherein the cardiac output (CO) corresponds to $$CO = Q_b \times \left[ \frac{(S_{ecmo}CO_{2(1)} - S_{ecmo}CO_{2(2)})}{(S_aCO_{2(1)} - S_aCO_{2(2)})} - 1 \right],$$

wherein $Q_b$ is the first blood flow rate; $S_{ecmo}CO_{2(1)}$ is a carbon dioxide content in blood delivered to the patient after passing the oxygenator at the first exchange rate; $S_{ecmo}CO_{2(2)}$ is a carbon dioxide content in blood delivered to the patient after passing the oxygenator at the second exchange rate; $S_aCO_{2(1)}$ is an arterial carbon dioxide content corresponding to the first exchange rate and $S_aCO_{2(2)}$ is an arterial carbon dioxide content corresponding to the second exchange rate.

9. A method for calculating cardiac output of a patient undergoing veno-arterial extracorporeal blood oxygenation, the method comprising:
  (a) establishing a first blood flow rate in an extracorporeal blood oxygenation circuit from a venous portion of a patient circulation system into an arterial portion of the patient circulation system;
  (b) measuring the first blood flow rate;
  (c) establishing a first exchange rate of a gas with the blood in the extracorporeal blood oxygenation circuit;
  (d) measuring a first value of a blood parameter in the arterial portion of the patient circulation system corresponding to the first exchange rate;
  (e) measuring a first value of the blood parameter in the blood delivered to the patient corresponding to the first exchange rate;
  (f) establishing a second exchange rate of the gas with the blood in the extracorporeal blood oxygenation circuit;
  (g) measuring a second value of the blood parameter in the arterial portion of the patient circulation system corresponding to the second exchange rate;
  (h) measuring a second value of the blood parameter in the blood delivered to the patient corresponding to the second exchange rate; and
  (i) calculating a cardiac output of the patient corresponding to the first blood flow rate and (x) the first value of a blood parameter in an arterial portion of the patient circulation system corresponding to the first exchange rate, (xx) the first value of the blood parameter in the blood delivered to the patient corresponding to the first exchange rate, (y) the second value of the blood parameter in the arterial portion of the patient circulation system corresponding to the second exchange rate and (yy) the second value of the blood parameter in the blood delivered to the patient corresponding to the second exchange rate.

10. The method of claim 9, wherein the gas is carbon dioxide.

11. The method of claim 9, wherein measuring the first blood flow rate is provided by a pump in the extracorporeal blood oxygenation circuit.

12. The method of claim 9, further comprising measuring the first value of the blood parameter in the blood delivered to the patient corresponding to the first exchange rate prior to the blood entering the patient circulation system.

13. The method of claim 9, further comprising measuring the second value of the blood parameter in the blood delivered to the patient corresponding to the second exchange rate prior to the blood entering the patient circulation system.

14. The method of claim 9, wherein measuring the first value of the blood parameter in the arterial portion of the patient circulation system corresponding to the first exchange rate includes measuring a first value surrogate parameter.

15. The method of claim 9, wherein measuring the second value of the blood parameter in the arterial portion of the patient circulation system corresponding to the second exchange rate includes measuring a second value surrogate parameter.

16. An apparatus for quantifying a cardiac output of a patient operably connected to an extracorporeal blood oxygenation circuit, the extracorporeal blood oxygenation circuit having an access line withdrawing blood from the circulation system of the patient, a blood oxygenator, a pump and a return line returning oxygenated blood to an arterial portion of the circulation system, the apparatus comprising:
  (a) a controller configured to connect to one of the blood oxygenator or the pump, the controller configured to calculate a cardiac output of the patient based on a measured first flow rate of oxygenated blood from the extracorporeal circuit, a first arterial carbon dioxide content or surrogate and a first carbon dioxide content or surrogate measured during a first flow rate of sweep gas though an oxygenator in the extracorporeal circuit; and a second arterial carbon dioxide content or surrogate and a second carbon dioxide content or surrogate measured during a second flow rate of sweep gas though the oxygenator in the extracorporeal circuit.

17. The apparatus of claim 16, wherein the controller calculates the cardiac output (CO) according to $$CO = Q_b \times \left[ \frac{(S_{ecmo}CO_{2(1)} - S_{ecmo}CO_{2(2)})}{(S_aCO_{2(1)} - S_aCO_{2(2)})} - 1 \right],$$

wherein $Q_b$ is the first blood flow rate; $S_{ecmo}CO_{2(1)}$ is a carbon dioxide content in blood delivered to the patient after passing the oxygenator at the first exchange rate; $S_{ecmo}CO_{2(2)}$ is a carbon dioxide content in blood delivered to the patient after passing the oxygenator at the second exchange rate; $S_aCO_{2(1)}$ is an arterial carbon dioxide content corresponding to the first exchange rate and $S_aCO_{2(2)}$ is an arterial carbon dioxide content corresponding to the second exchange rate.

\* \* \* \* \*